(12) United States Patent
Pylkkanen

(10) Patent No.: US 10,101,210 B2
(45) Date of Patent: Oct. 16, 2018

(54) PORTABLE ANALYZER AND METHOD FOR DETERMINING A COMPOSITION OF A SAMPLE

(71) Applicant: Oxford Instruments Industrial Products Ltd.

(72) Inventor: Tuomas Pylkkanen, Helsinki (FI)

(73) Assignee: Hitachi High-Tech Analytical Science Limited, Oxfordshire (GB)

( * ) Notice: Subject to any disclaimer, the term of this patent is extended or adjusted under 35 U.S.C. 154(b) by 0 days.

(21) Appl. No.: 15/359,759

(22) Filed: Nov. 23, 2016

(65) Prior Publication Data

US 2017/0146404 A1    May 25, 2017

(30) Foreign Application Priority Data

Nov. 24, 2015 (EP) .................................... 15196012

(51) Int. Cl.
*G01J 3/443* (2006.01)
*G01J 3/02* (2006.01)
(Continued)

(52) U.S. Cl.
CPC ............. *G01J 3/443* (2013.01); *G01J 3/0208* (2013.01); *G01J 3/0272* (2013.01); *G01J 3/10* (2013.01); *G01J 3/45* (2013.01)

(58) Field of Classification Search
CPC .. G01J 3/443; G01J 3/10; G01J 3/0208; G01J 3/0272; G01J 3/45
See application file for complete search history.

(56) References Cited

U.S. PATENT DOCUMENTS

2007/0296967 A1    12/2007   Gupta et al. ................... 356/318
2008/0018890 A1*   1/2008   Maity ....................... G01J 1/44
                                                                  356/301
(Continued)

FOREIGN PATENT DOCUMENTS

WO    WO 2008/103937 A2    8/2008

OTHER PUBLICATIONS

Pu, Tongni, et al., "A Microfabricated ICP Source and its Application in Miniaturization of Spectrometer", IEEE 2010, pp. 336-338.
(Continued)

*Primary Examiner* — Michael P Lapage
(74) *Attorney, Agent, or Firm* — Harrington & Smith

(57) ABSTRACT

A portable analyzer determines composition of a sample and includes excitation means for invoking an optical emission from a surface of the sample, detector means for observing a selectable wavelength in said optical emission and for recording a detection signal that is descriptive of at least one characteristic of said optical emission at a selected wavelength, analysis means for determination of elemental composition of the sample on basis of one or more detection signals; and control means for carrying out a spectral analysis by operating the excitation means to generate the optical emission for recording respective detection signals at predefined wavelengths, operating the detector means to record the respective one or more detection signals at said one or more predefined wavelengths, and operating the analysis means to determine elemental composition of the sample on basis of said recorded detection signals.

11 Claims, 5 Drawing Sheets

(51) Int. Cl.
  *G01J 3/45* (2006.01)
  *G01J 3/10* (2006.01)

(56) References Cited

U.S. PATENT DOCUMENTS

| | | | | |
|---|---|---|---|---|
| 2012/0033220 | A1* | 2/2012 | Kotidis | B82Y 20/00 |
| | | | | 356/445 |
| 2012/0062874 | A1* | 3/2012 | Beckstead | G01J 3/02 |
| | | | | 356/72 |
| 2013/0341509 | A1* | 12/2013 | Nelson | G01J 3/0248 |
| | | | | 250/330 |
| 2015/0185081 | A1* | 7/2015 | Sano | G01J 3/0272 |
| | | | | 356/456 |
| 2015/0233762 | A1* | 8/2015 | Goldring | G01J 3/108 |
| | | | | 356/451 |

OTHER PUBLICATIONS

Baldwin, David P., et al., "High-Resolution Spectroscopy Using an Acousto-Optic Tunable Filter and a Fiber-Optic Fabry-Perot Interferometer", Applied Spectroscopy vol. 50, No. 4, 1996, pp. 498-503.

* cited by examiner

PORTABLE ANALYZER AND METHOD FOR DETERMINING A COMPOSITION OF A SAMPLE

TECHNICAL FIELD

The present invention relates to a portable analyzer device for analysis of sample composition. In particular, embodiments of the present invention relate to providing such a portable analyzer that is small in size.

BACKGROUND

Handheld or otherwise portable analyzer devices are frequently used in the field e.g. for recognizing and sorting objects according to material(s) they contain. As a few examples, a portable analyzer device may be used in places like scrapyards, dumping grounds and recycling centers. While several techniques for analyzing a sample under study are available, optical emission spectroscopy is widely employed in portable analyzer devices to determine elemental composition of the sample under study. Such analyzer devices may be referred to as optical analyzers. An optical analyzer typically includes an excitation means for invoking an optical emission from a surface of a sample under study, a detector means for capturing signals that are descriptive of the optical emission and an analysis means for determination of the elemental composition of the sample under study on the basis of the captured signals.

A well-known example of such an optical analyzer employs laser-induced breakdown spectroscopy (LIBS) and may be referred to as a LIBS analyzer. A LIBS analyzer comprises, as the excitation means, a laser that is arranged to generate a high peak power laser pulse. The laser pulse is focused to the sample under study to form a plasma plume on a surface of the sample in order to cause atomization and excitation on the surface. This causes light emission at wavelength(s) that are characteristic to elements on the surface of the sample. The light emission is received at the detector means, which then carries out an analysis based on the received optical emission from the sample to determine the elemental composition of the sample. Since all elements emit light that exhibit wavelength(s) characteristic thereto, the relative intensities of different wavelengths in the light received at the detector means reveal the elemental constitution of the sample.

A dominant design of the detector means in a LIBS analyser, or in any optical analyser, makes use of a Czerny-Turner spectrometer known in the art. In a Czerny-Turner spectrometer the received light emission is transferred to an array detector via an optical path that involves one or more dispersing elements. FIG. 1 schematically illustrates an example that depicts operating principle of a Czerny-Turner spectrometer 100. The spectrometer 100 is shown with an entrance slit 102, a collimating mirror 104, a diffraction element 106, a focusing mirror 108 and an array detector 110. The diffraction element 106 may comprise e.g. a diffraction grating or a diffraction prism. In operation, the light entering via the entrance slit 102 hits the collimating mirror 104, from which collimated light is reflected to the diffraction element 106. The diffracted light from the diffraction element 106 hits the focusing mirror 108, from which the diffracted light is reflected to the array detector 110. The array detector 110 records signals that represent relative light intensities at different wavelengths, and these signals are provided for analysis to identify the element(s) that match the recorded relative light intensities. The route of the received light from the entrance slit 102 to the array detector 110 may be referred to as an optical path of the spectrometer 100.

Characteristics and relative positions of optical components of the spectrometer 100, i.e. the entrance slit 102, the collimating mirror 104, the diffraction element 106, the focusing mirror 108 and the array detector 110, define the range of wavelengths the spectrometer 100 is able to consider in the analysis. While such spectrometer can be applied for high-quality analysis, due to physical characteristics of the optical components of the spectrometer required to reach a sufficient range of wavelengths, the optical path defined by the optical components of the spectrometer 100 cannot be made arbitrarily short. In particular, the operation of the diffraction element 106 typically requires a certain minimum length for the optical path. In other words, the minimum size of the portable analyser employing the spectrometer 100 is limited due to the length of the optical path. On the other hand, having a portable analyser device of as small size as possible would be preferred to make the handling of the analyser device more convenient for the user and also to enable using the analyser device in narrow spaces when required.

SUMMARY

It is therefore an object of the present invention to provide a portable analyzer device that is small size while providing good analysis performance.

In the following, a simplified summary of some embodiments of the present invention is provided in order to facilitate a basic understanding of a portable analyzer according to various embodiments of the present invention. The summary is, however, not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

According to an example embodiment, a portable analyzer for determining composition of a sample is provided, the analyzer comprising an excitation means for invoking an optical emission from a surface of the sample, a detector means for observing a selectable wavelength in said optical emission and for recording a detection signal that is descriptive of at least one characteristic of said optical emission at a selected wavelength, an analysis means for determination of elemental composition of the sample on basis of one or more detection signals; and a control means for carrying out a spectral analysis. The control means is arranged to carry out the spectral analysis by operating the excitation means to generate the optical emission for recording respective one or more detection signals at one or more predefined wavelengths, operating the detector means to record the respective one or more detection signals at said one or more predefined wavelengths, and operating the analysis means to determine elemental composition of the sample on basis of said recorded detection signals.

According to another example embodiment, a method for determining composition of a sample by using an excitation means for invoking an optical emission from a surface of the sample and a detector means for observing a selectable wavelength in said optical emission and for recording a detection signal that is descriptive of at least one characteristic of said optical emission at a selected wavelength is provided, the method comprising operating the excitation means to generate the optical emission for recording respective one or more detection signals at one or more predefined wavelengths, operating the detector means to record the respective one or more detection signals at said one or more predefined wavelengths, and determining elemental composition of the sample on basis of said recorded detection signals.

According to another example embodiment, a computer program for determining composition of a sample is provided, the computer program comprising computer readable program code configured to cause performing the method according to an example embodiment when said program code is run on a computing apparatus.

The computer program referred to above may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF DRAWINGS

In the accompanying drawings.

DETAILED DESCRIPTION

Figure 1:
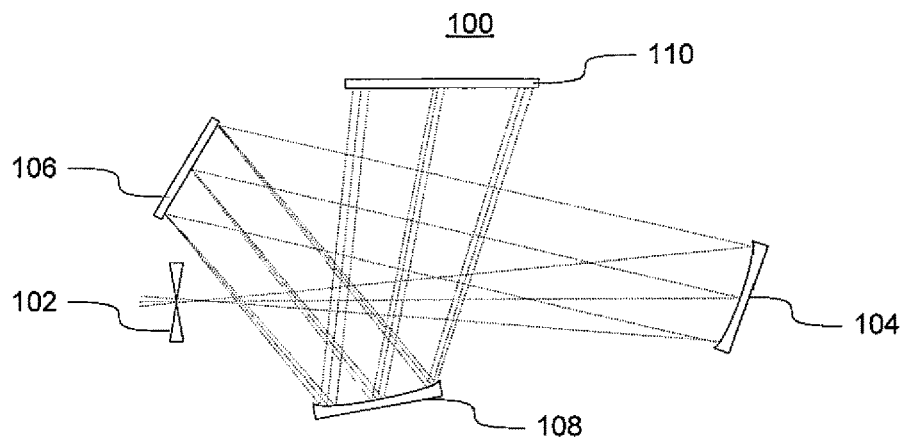
FIG. 1 schematically illustrates an operating principle of a Czerny-Turner spectrometer.
Figure 2:
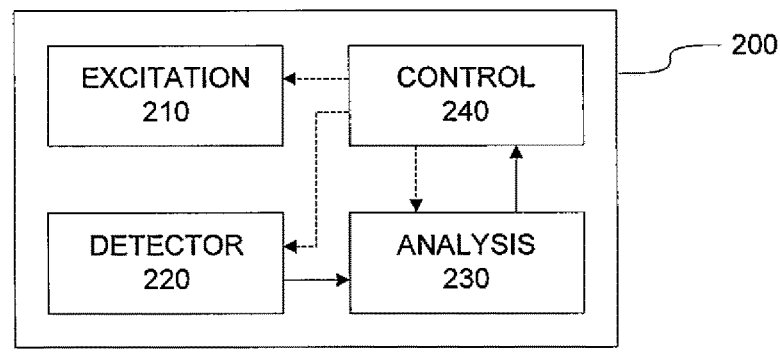
FIG. 2 schematically illustrates some components of a portable analyser according to an example embodiment.

FIG. 2 schematically illustrates some components of a portable analyser 200 for the analysis of sample composition. In this example, the portable analyser 200 comprises an excitation means 210 for invoking an optical emission from a surface of a sample under study, a detector means 220 for observing a selectable wavelength in the optical emission and for recording a detection signal that is descriptive of one or more characteristics of the optical emission so invoked at a selected wavelength, analysis means 230 for determination of elemental composition of the sample under study on basis of one or more recorded detection signals, and control means 240 for operating the excitation means 210, the detector means 220 and the analysis means 230 to carry out a spectral analysis to determination of the elemental composition of the sample under study. The control means 240 is communicatively coupled (e.g. by one or more electrical wires or electrical connectors of other type) to the excitation means 210, to the detector means 220 and to the analysis means 230 to enable control these components. In the example of FIG. 2, the dashed lines denote control signals and solid lines denote flow of (other) information. In other examples, the analysis means 230 may be, at least in part, integrated to the detector means 220 and/or to the control means 240.

As described in the foregoing, the detector means 220 is arranged to observe a selectable wavelength and it is also arranged to record a detection signal that is descriptive of one or more characteristics of the optical emission at a selected wavelength. In other words, the detector means 220 serves as wave-length-selective (or frequency-selective) detector that is tunable or adjustable to observe optical emission at a wavelength of interest while ignoring other wavelengths. The one or more characteristics of the optical signal captured in the detection signal may comprise e.g. an indication of presence or absence of the specified wavelength in the optical emission received at the detector means 220, an indication of probability of presence of the specified wavelength in the optical emission received at the detector means 220 and/or an indication of (relative) intensity of the specified wavelength in the optical emission received at the detector means 220.

In this regard, the detector means 220 is adjustable to observe a wavelength of interest. In an example, the adjustment may enable freely selecting a wavelength between predefined minimum and maximum wavelengths. In another example, the adjustment may enable selecting one of two or more predefined wavelengths. The adjustment may be carried under control of an adjustment signal issued by the control means 240. In an example, the adjustment signal carries an indication that results in adjusting the detector means 220 to observe a selected (or desired) wavelength. In another example, the adjustment signal carries an indication that results in a desired change in wavelength to be observed. While referred herein to as a wavelength in singular for editorial clarity of the description, the detector means 220 adjusted to observe a certain wavelength is in practice typically arranged to observe (a relatively narrow) range of wavelengths centered at the certain wavelength. As an example, in a scenario where the detector means 220 is arranged to provide a relatively low resolution, the range may be a few tens of nanometers, whereas in case the detector means 220 is arranged to provide a relatively high resolution the range may in the order of 1 nanometer or even less. In another example, the range may depend on the center wavelength, e.g. such that the range is in the order of ±10% of the center wavelength (a low-resolution scenario) or such that the range is in the order of <1% of the center wavelength (a high-resolution scenario).

Figure 3:
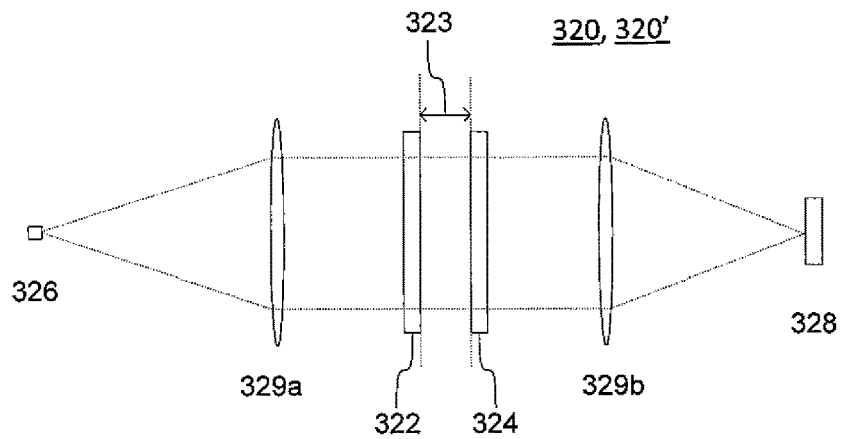
FIG. 3 schematically illustrates an example of a Fabry-Pérot interferometer.

In an example, the detector means 220 is arranged to employ Fabry-Pérot interferometer (FPI) known in the art. FIG. 3 schematically illustrates some components of a FPI 320 to facilitate an overview of its operating principle. The FPI 320 comprises a pair of optical flats including a first optical flat 322 and a second optical flat 324 that are arranged in parallel or substantially in parallel with each other. The surface of the first optical flat 322 facing the second optical flat 324 may be referred to as the front surface of the first optical flat 322, whereas the opposite surface of the first optical flat 322 may be referred to as a rear surface of the first optical flat 322. Along similar lines, the surface of the second optical flat 324 facing the first optical flat 322 may be referred to as the front surface of the second optical flat 324, whereas the opposite surface of the second optical flat 324 may be referred to as a rear surface of the second optical flat 324. The first and second optical flats 322, 324 are arranged such that there is an air gap 323 between the front surfaces of the optical flats 322, 324. In a variation of the FPI 320, each of the first and second optical flats 322, 324 have a wedge-like shape to avoid reflections from the back surfaces thereof that could otherwise cause disturbances in the detection signals and could hence compromise the accuracy of the spectral analysis.

The first and second optical flats 322, 324 consist of glass or other transparent material, and their front surfaces are at least partially reflective. According to an example, the first and second optical flats 322, 324 are provided as respective plates or discs made of glass or transparent plastic with their front surfaces that are facing each other constituting respective mirrors. The back surfaces of the first and second optical flats 322, 324 may have an anti-reflective coating or a coating that at least reduces reflections therefrom in order to avoid undesired reflections from the back surfaces that could compromise the spectral analysis due to disturbances they may cause in the detection signals. Instead of applying a coating, the reflectivity of the back surfaces may be reduced or eliminated by using some other means known in the art.

In FIG. 3 the FPIs 320 is further illustrated with a point-like light source 326 and a light detector 328 as well as with a collimating lens 329a between the light source 326 and the first optical flat 322 and an optional focusing lens 329b between the second optical flat 324 and the light. A ray of incoming light from the light source 326 enters, via the collimating lens 329a, the pair of first and second optical flats 322, 324 through the rear surface of the first optical flat 322, it is multiply reflected between the front surfaces of the first and second optical flats 322, 324, it exits the pair of the first and second optical flats 322, 324 through the rear surface of the second optical flat 324, and hits the light detector 328 through the optional focusing lens 329b.

In an example, the focusing lens 329b may be excluded from the FPI 320 in case the light detector 328 has an area that is not smaller than the area of the pair of the first and second optical flats 322, 324. On the other hand, the focusing lens 329b is typically needed in case the light detector 328 has an area that is smaller than the area of the pair of the first and second optical flats 322, 324. The light received in the FPI 320, 320' via the light source 326 may originate from the optical emission invoked on the surface of the sample under study by operation of the excitation means 210, whereas light intensity captured by the light detector 328 is converted into the detection signal for provision to the analysis means 230.

The pair of the first and second optical flats 322, 324 result in a transmission spectrum with one or more local maxima that depend on the width of the air gap 323 between the first and second optical flats 322, 324. Therefore the width of the air gap 323 between the first and second optical flats 324, 324 defines the wavelength(s) of light that may be detected by the light detector 328. These wavelengths include a primary wavelength and its harmonics. In other words, employing a certain width for the air gap 323 results in the light detector 328 capturing light intensities of the light received via the light source 326 at wavelengths that correspond to the certain width of the air gap 323. Hence, the certain width of the air gap 323 may be applied, for example, to determine presence or absence of one or more of the corresponding wavelengths in the light received via the light source 326 or to determine (relative) light intensities at one or more of the corresponding wavelengths.

The collimating lens 329a serves to ensure that the light entering the pair of optical flats 322, 324 is collimated or substantially collimated, in other words to ensure that the rays of light that enter the pair of optical flats 322, 324 are parallel or substantially parallel to each other. In the FPI 320 the collimated light enters the pair of optical flats 322, 324 in a direction that is perpendicular or substantially perpendicular to the (front and back) surfaces of the first optical flat 322, in other words the rays of light meet the back surface of the first optical flat 322 in an incidence angle θ that is equal to or substantially equal to 0 degrees. In a variation of the FPI 320, the light source 326 and the collimating lens 329a may be arranged with respect to the pair of optical flats 322, 324 such that the light enters the back surface of the first optical flat 322 in an incidence angle θ that is substantially different from 0 degrees. This affects the transmission spectrum of the FPI 320 as will be described in more detail in the following.

In another variation of the FPI 320, the collimating lens 329a may be replaced by a collimating mirror, where the light source 326 and the collimating mirror are arranged such that they cause collimated light to enter the back surface of the first optical flat 322 in a desired incidence angle θ. Note that in the collimating lens 329a and the collimating mirror serve as examples of a collimating optical component that may be employed to arrange the collimated light entering the back surface of the first optical flat 322 in a desired incidence angle θ.

In a further variation of the FPI 320, a focusing mirror may be used instead of the focusing lens 329b to cause the light exiting from the pair of optical flats 322, 324 to hit the light detector 328. Herein, the focusing lens 329b and the focusing mirror serve as examples of an optional focusing optical component that may be employed to arrange the light exiting the pair of optical flats 322, 324 to hit the light detector 328.

As pointed out in the foregoing, the wavelengths transmitted through the pair of first and second optical flats 322, 324 include the primary wavelength that directly depends on the width of the air gap 323 and its harmonics.

In general, the relationship between the transmission spectrum and characteristics of a pair of optical flats forming the 'core' of a FPI may be characterized using the following equation:

$$\lambda = \frac{2*n*d*\cos\theta}{m},$$

wherein λ denotes the wavelength of a local maxima in the transmission spectrum n denotes the refractive index of the material between the front surfaces of the optical flats that constitute the 'core' of the FPI, d denotes the width of the gap between the optical flats, θ denotes the incidence angle (described in the foregoing), and m is a positive integer that denotes transmission order of the FPI. In consideration of the FPI 320, the refractive index for air is 1 and hence for the air gap 323 of the FPI 320 we use n=1. Moreover, due to the light entering the pair of optical flats 322, 324 in an incidence angle θ that is 0 degrees or substantially 0 degrees, the term cos θ equals or substantially equals 1, and the above equation reduces into $$\lambda = \frac{2*d}{m}.$$

Figure 4:
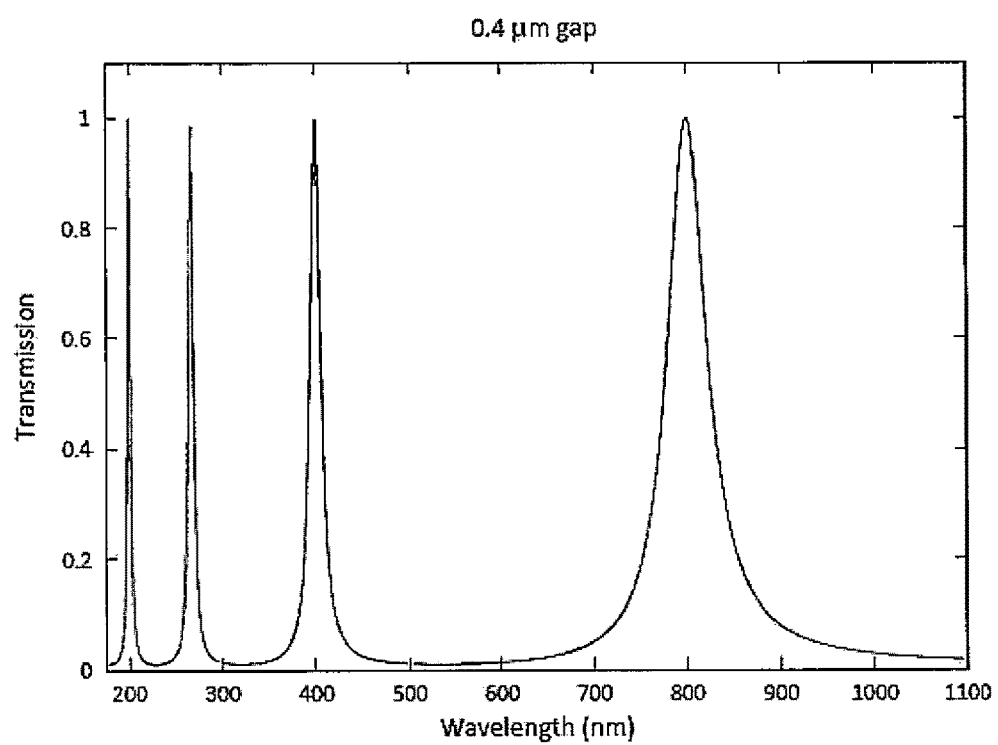
FIG. 4 depicts an example of a transmission spectrum obtainable using a Fabry-Pérot interferometer.

FIG. 4 illustrates an example of the transmission spectrum for the FPI 320 where the air gap 323 is set to 0.4 μm, which results in local maxima of the transmission spectrum e.g. at wavelengths 800 nm (for m=1, representing the primary wavelength), 400 nm (for m=2, representing the first harmonic wavelength), approx. 267 nm (for m=3, representing the second harmonic wavelength) and 200 nm (for m=4, representing the third harmonic wavelength). Herein, the abbreviation μm stands for micrometers and the abbreviation nm stands for nanometers.

In an example, the subsequent analysis by the analysis means 230 may consider a plurality of the primary wavelength and the harmonic wavelengths of the transmission spectrum of the FPI 320, e.g. the primary wavelength together with a predefined number of harmonic wavelengths or a predefined set of harmonic wavelengths. In another example, the subsequent analysis by the analysis means 230 may consider only the primary wavelength or only one of the harmonic wavelengths of the transmission spectrum of the FPI 320. In some scenarios, one or more of the primary wavelength and the harmonic wavelengths that are not to be considered by the analysis means 230 may result in disturbances that may degrade the quality of the analysis. To account for such a scenario, the possible detrimental effect of the harmonic wavelengths that are of no interest in the analysis of the sample composition may be mitigated, for example, by combining the FPI 320 with any of (1) a band-pass filter that only allows transmitting wavelengths in a predefined FPI operating range, (2) a combination of a low-pass filter and a high-pass filter having the same or similar effect as the bandbass filter of the option (1), or (3) an additional lower-resolution FPI that is arranged to operate as a band-pass filter of desired characteristics.

The width of the air gap 323 between the first and second optical flats 322, 324 may be adjustable under control of the control means 240. In this regard, one or both of the first and second 322, 324 may be moveable such that they can be brought closer to each or further away from each other in accordance with an adjustment signal issued by the control means 240. The movement of one or both of the optical flats 322, 324 may be enabled using a suitable technique known in the art, e.g. by micro-electro-mechanical system (MEMS) based actuator(s) or by piezo-based actuators coupled thereto, which actuators are responsive to the adjustment signal. In an example, the adjustment of the width of the air gap 323 may enable freely setting the gap width to a desired width between predefined minimum and maximum widths. In another example, the adjustment between the maximum and minimum widths may be made in steps of predefined length. The minimum and maximum widths may be set or selected in accordance with the wavelengths that are required for the analysis of the sample composition in the analysis means 230.

The control means 240 may have access to a mapping between available wavelengths (e.g. the range of wavelengths between the predefined minimum and maximum wavelengths or two or more predefined wavelengths) and corresponding gap widths between the first and second optical flats 322, 324 of the FPI 320. Upon issuing the adjustment signal, the control means 240 may employ the mapping to transform the desired wavelength into the corresponding gap width or to transform the desired change in the wavelength into corresponding change in the gap width and use this transformed piece of information in the issued adjustment signal.

The FPI 320 that has been described herein in a number of details serves as an example of the detector means 220 that is capable of observing a selectable wavelength of interest. However, this is a non-limiting example and a detector of other type can be employed instead. As another example in this regard, the detector means 220 may comprise a tunable optical bandpass filter, such as an acousto-optical tunable filter (AOTF), a liquid-crystal tunable filter (LCTF), or an angle-tuned thin film filter, in combination with a light detector.

The excitation means 210 may comprise a laser source that is arranged to generate a series of one or more laser pulses under control of a trigger signal issued by the control means 240. In case the excitation means 210 comprises the laser source for this purpose, the portable analyzer 200, 200' may be referred to as a portable laser-induced breakdown spectroscopy (LIBS) analyzer. The trigger signal that initiates generation of the laser pulse(s) in the excitation means 210 may specify characteristics of the laser pulse(s), e.g. the number of pulses to be generated, repetition rate/frequency of the pulses to be generated (if more than one pulses are to be generated) and/or power/energy of the pulse(s) and the excitation means 210 may control the laser source accordingly. Moreover, the trigger signal may further specify characteristics such as duration of the pulse(s), wavelength (s) to be applied in the pulse(s), bandwidth of the pulse(s) and the excitation means 210 may include mechanism(s) for adjusting the pulses accordingly.

Instead of the trigger signal indicating characteristics of the series of one or more laser pulses to be generated, some or all of the pulse generation characteristics applied by the laser source of the excitation means 210 may be predefined. As an example, the trigger signal may cause the laser source to generate a series including a predefined number of pulses at a predefined energy/power using a predefined bandwidth and wavelengths, where the pulses have predefined duration at a predefined repetition rate.

Instead of relying on a laser-based excitation that involves usage of the laser source for generation of laser pulses, the excitation means 210 may apply an excitation source of other type known in the art. Non-limiting examples in this regard include spark-based or arc-based excitation techniques known in the art of optical emission spectroscopy, glow discharge, inductively coupled plasma atomic emission spectroscopy (ICP-AES), microwave-assisted excitation in combination with one of the spark-based excitation, arc-based excitation and laser-based excitation.

The control means 240 is arranged to operate the excitation means 210, the detector means 220 and the analysis means 230 to carry out the spectral analysis in response to an initiation signal. The initiation signal may be received e.g. in response to the user operating the trigger means of the portable analyzer 200, 200'.

In particular, the spectral analysis involves the control means 240 operating the excitation means 210 and the detector means 220 to record a plurality of detection signals, each detection signal representing light captured with the detection means 220 adjusted to observe a different, predefined wavelength. In this, regard, the control means 240 may apply a predefined sequence of wavelengths. In order to record the respective detection signal for each wavelength of the sequence, the control means 240 scans over the wavelengths defined in the sequence.

Figure 5:
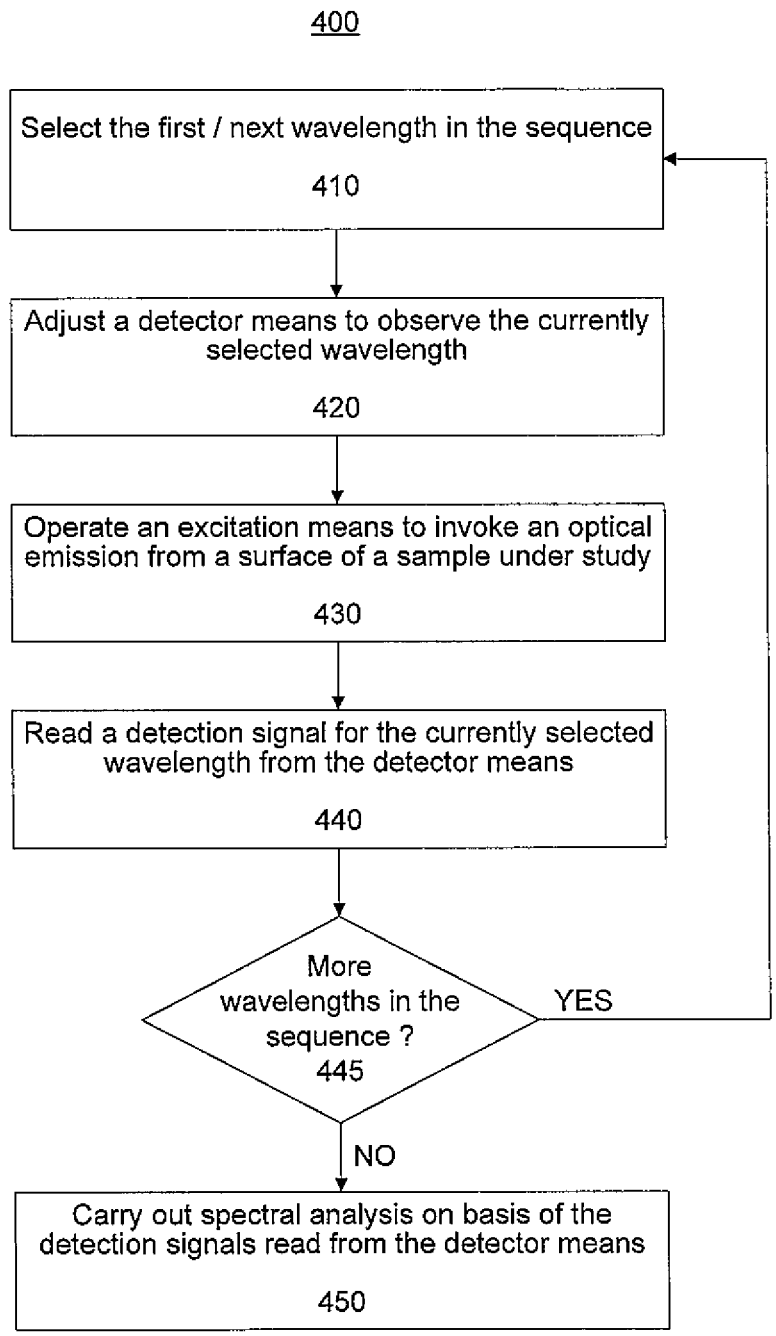
FIG. 5 depicts a flowchart illustrating a method according to an example embodiment.

As an example, the scanning procedure may carried out according to a method 400 illustrated by a flowchart in FIG. 5. For each wavelength of the sequence, the control means 240 selects the first or the next wavelength of the sequence, as indicated in block 410 and adjusts the detector means 220 to observe this wavelength, as indicated in block 420. The adjustment may be carried out by the control means 240 issuing the adjustment signal, as described in the foregoing. In block 430, the control means 240 operates the excitation means 210 to invoke an optical emission from a surface of a sample under study, which results in the detector means 220 recording the respective detection signal. This may be accomplished by the control means 240 issuing a trigger signal, as described in the foregoing. In block 440, the control means 240 reads a respective detection signal, in other word the detection signal for the currently selected wavelength, from the detector means 220.

In block 445 the control means 240 verifies whether there are more wavelengths in the sequence to be scanned. If the verification of block 445 is affirmative, the operations of blocks 410 to 445 are repeated. If the verification of block 445 is non-affirmative, the scanning over the sequence of wavelengths is complete and the method 400 proceeds to carry out the spectral analysis to determine elemental composition of the sample under study on basis of the detection signals recorded in the scanning loop (of blocks 410 to 440), as indicated in block 450. The result of the analysis may be displayed to the user via a display means provided in the portable analyzer 200, 200' and/or stored in a memory or a mass storage device accessible by the portable analyzer 200, 200' for subsequent viewing and/or other use.

As described in the foregoing, the invocation of the optical emission may be provided using a laser-based excitation means. In such an example, the operation referred to in blocks 430 and 440 for a single wavelength of the sequence may include controlling the laser source in the excitation means 210 to generate a sub-series of laser pulses and reading, from the detector means 220, the respective detection signal that is descriptive of the optical emission invoked by the respective sub-series of laser pulses. In general, the sub-series of laser pulses includes a predefined number of pulses, e.g. just a single laser pulse or a predefined number (that is larger than one) of laser pulses. In the former case the respective detection signal is descriptive of the optical emission invoked by the respective single laser pulse, whereas in the latter case the respective detection signal is descriptive of the average optical emission over the predefined number of laser pulses.

In an example, laser pulses of similar or substantially similar characteristics may be employed across the wavelengths of the sequence. This approach may be useable to ensure that the wavelengths of the sequence are analyzed on basis of the same or similar optical spectrum. In another example, one or more characteristics of the laser pulse may be adjusted in dependence of the wavelength under analysis. This approach may be useable e.g. in order to enable optimizing the analysis performance by employing, for a given wavelength of the sequence, laser pulses of a type that are especially suitable for analysis of the given wavelength.

The sequence of wavelengths may, for example, include wavelengths from a predefined minimum wavelength to a predefined maximum wavelength at predefined intervals. As another example, the sequence may include an arbitrary set of one or more wavelengths. As a particular example of the latter, the set of one or more wavelengths may consist of wavelengths that are characteristic of a certain (e.g. user-selectable) element of interest. In a preferred example, the sequence includes or consists of wavelengths that represent the ultraviolet (UV) spectrum (approximately from 100 to 400 nanometers). In other examples, the sequence may comprise or consist of wavelengths that represent visible light spectrum (approximately from 400 to 700 nanometers), or the sequence may comprise or consist of wavelengths that represent infrared spectrum (approximately from 700 to 1000 nanometers).

Due to the operation of scanning of over the sequence of wavelengths, the portable analyzer 200, 200' may be referred to as a scanning spectrometer or as a scanning analyzer. In contrast, a non-scanning analyzer, such as one making use of a Czerny-Turner spectrometer, may be able to capture characteristics of the optical emission from the sample under study at a full range of wavelengths of interest in one go (e.g. based on a single detection signal). While a scanning operation applied in the portable analyzer 200, 200' may result in an analysis procedure that takes slightly longer in comparison to that of a non-scanning analyzer, the portable analyzer 200, 200' enables usage of simpler (and hence more durable and more affordable) components in the detector means 220 and also enables providing an analyzer device of smaller size in comparison to non-scanning analyzers while still enabling uncompromised analysis quality.

In the examples described in the foregoing, an implicit assumption has been that the portable analyzer 200 comprises a single detector means 220. In other examples, the portable analyzer 200 may comprise multiple (e.g. two or more) detector means 220 to enable speeding up the analysis. In such an arrangement, each of the multiple detector means 220 is adjustable to observe a respective wavelength of interest such that the wavelength to be observed is adjustable or selectable independently of the other detector means 220. In such a scenario the multiple detector means 220 are arranged to operate simultaneously or substantially simultaneously to provide respective detection signals from more than one pre-selected wavelength during the same measurement time, thereby enabling faster analysis in comparison to a scenario where only a single detector means 220 is employed. Such operation can also further improve the accuracy of the final result since multiple wavelengths are observed or measured simultaneously from the same optical emission event(s). Due to the potentially very small size of the detector means 220, providing the portable analyzer 200 with multiple detector means 220 would not significantly increase the size of the portable analyzer device.

In an example, the portable analyzer 200 operation when multiple detector means 220 are available there may involve allocating the sequence of wavelengths described above to the multiple detector means 220 such that each of the multiple detector means 220 is assigned a respective sub-sequence of the overall wavelength sequence. This way, a plurality of detection signals, each corresponding to a different wavelength, may be read simultaneously to enable faster scanning of the wavelengths sequence of interest. In another example, the portable analyzer 200 operation in case of multiple detector means 220 may be carried out such that one or more detector means 220 may be adjusted to observe respective one or more wavelengths that are characteristic to a pre-selected analyte (e.g. chromium), while the analysis means 230 may be arranged to consider the respective detection signals in an attempt to detect the pre-selected analyte. In parallel, at least one detector means 220 may be arranged to observe a so-called matrix element that is present in majority in the sample (e.g. iron in the case of steel), while the analysis means 230 may be arranged to consider the respective detection signal(s) in an attempt to detect the matrix element.

In consideration of the method 400 in a scenario where the portable analyzer 200 includes multiple detector means 220, the method is carried out in a slightly different manner, as outlined in the following.

In block 410, the first/next wavelength in the sequence is selected for each of the multiple detector means 220;

In block 420, each of the detector means 220 is adjusted to observe respective currently selected wavelength; and In block 440, the detection signals are read from each of the multiple detector means 220.

There is a plurality of ways to provide a portable analyzer device hosting the components of the portable analyzer 200, 200'. In this regard, FIGS. 6A, 6B, 7A and 7B illustrate respective non-limiting example of arranging some components of the portable analyzer 200, 200' in a casing.

Figure 6A:
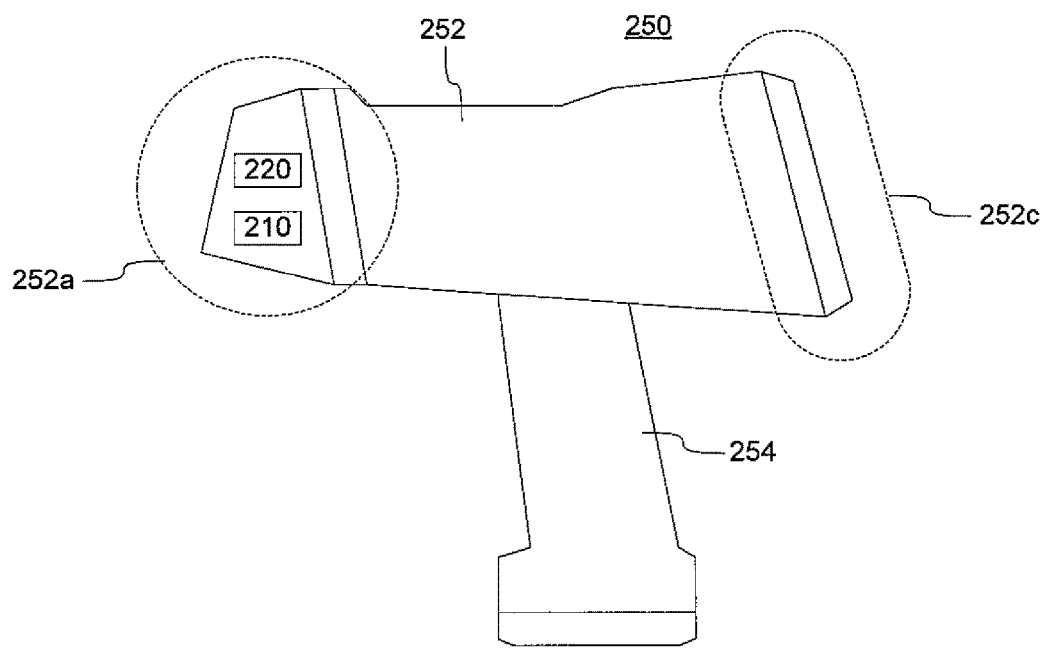
FIGS. 6A and 6B schematically illustrate respective examples of arranging some components of a portable analyzer into a casing.

The illustration of FIG. 6A schematically depicts a side view to the casing 250, which, at least conceptually, includes two parts: a body 252 for housing the excitation means 210 and the detector means 220 and a handle 254 for holding the portable analyzer 200 when it is in use. When using the portable analyzer 200, the user typically grabs the handle 254 with one hand and points a front part 252a of the body 252 away from the user, against or close to the object under analysis. Therefore, in the portable analyzer 200, both the excitation means 210 and the detector means 220 are arranged in the front part 252a to enable effective excitation of the object under analysis by the excitation means 210 and effective capturing of the optical emission invoked on the surface of the object under analysis by the detector means 220.

The portable analyzer 200 may further comprise a number of components that are typical for corresponding analyzers known in the art, including user input means for receiving input from a user and user output means for providing output to the user. The user input means may comprise, for example, one or more keys, buttons or knobs, a touchscreen, a touchpad, etc. to enable receiving user input to configure operating parameters of the portable analyzer 200 according to analysis task at hand. The output means may comprise a display means for displaying information to the user, such as e.g. an electronic visual display, a touchscreen, one or more light indicators (e.g. LEDs) etc. The display means may be employed, for example, to provide information concerning the result of the analysis, operational state of the portable analyzer and/or indication(s) regarding current settings of operating parameters of the portable analyzer 200. The output means may comprise, additionally or alternatively, a sound reproduction means for providing audible information to the use. The audible information may include, for example, sounds or signals that are descriptive of operational state of the portable analyzer, indication(s) regarding current settings of operating parameters of the portable analyzer 200 and/or initialization/completion of the analysis triggered by the user.

The portable analyzer 200 is typically also provided with a dedicated trigger means that enable the user to initiate analysis of the sample. Conceptually, the trigger means may be part of the user input means, although due to its special function it may be provided separately from main part of the user input means. In particular, the trigger means may be arranged in a front side of the handle 254 to make it readily accessible by the user e.g. by pressing it using the index finger of the hand holding the handle 254. The user input means and the user output means, to extent they are present in the analyzer device, are preferably arranged in the casing 250 such that they are conveniently accessible by the user when the portable analyzer 200 is in use, e.g. in an upper part of the body 252 and/or in the rear part 252c.

Figure 6B:
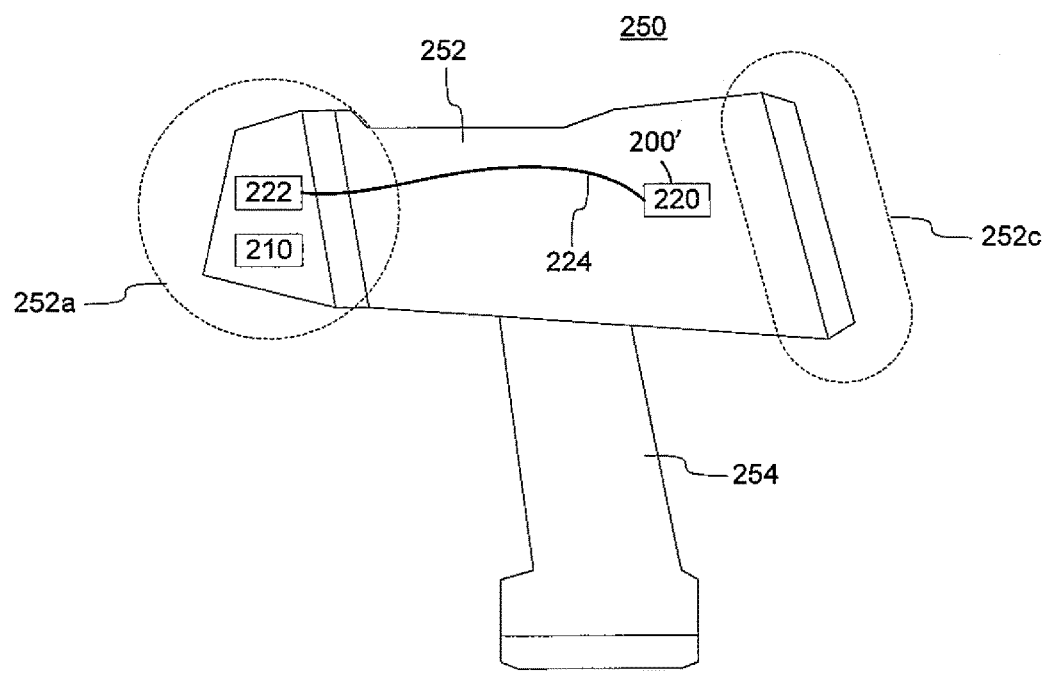

The illustration of FIG. 6B schematically depicts some components of a portable analyzer 200' that is variation of the portable analyzer 200. In the portable analyzer 200', the main difference to the portable analyzer 200 is the location of the detector means 220: instead of arranging the detector means 220 in the front part 252a, the detector means 220 is arranged closer to the rear part 252c of the body 252. In the portable analyzer 200', the front part 252a comprises an optical receiver 222 that is optically coupled to the detector means 220. In the illustration of FIG. 6B, the optical coupling is provided by an optical fiber cable 224, while other examples may employ different means of optical coupling. The optical receiver 222 may simply comprise an end of the optical fiber cable 224 (or an end of another means of optical coupling), which may be further covered by a lens or a transparent cover (made of for example diamond, sapphire, glass or plastic) for protection against dust, dirt and other impurities in the operating environment of the portable analyzer 200, 200'. The optical receiver 222 may also employ focusing optical elements such as mirrors or lenses to more efficiently collect and couple light into the detector means 220. In further variations of the portable analyzer 200, the detector means 220 may be arranged in any suitable location in the body 252 or e.g. in the handle 254.

Still referring to the illustrations on FIGS. 6A and 6B, each of the analysis means 230 and the control means 240 may be provided in any suitable location within the casing 250, either in the body 252 or in the handle 254. Regardless of details of the design of the casing 250 and arrangement of the excitation means 210, the detector means 220, the analysis means 230 and the control means 240 therein, the usage of the detector means 220 that employs the FPI enables a design that results in an analyzer device that in smaller in size in comparison to known portable analyzers that employ e.g. Czerny-Turner spectrometer or other detection means that involves usage of the diffraction element 106 without compromising its analysis performance.

Figure 7A:
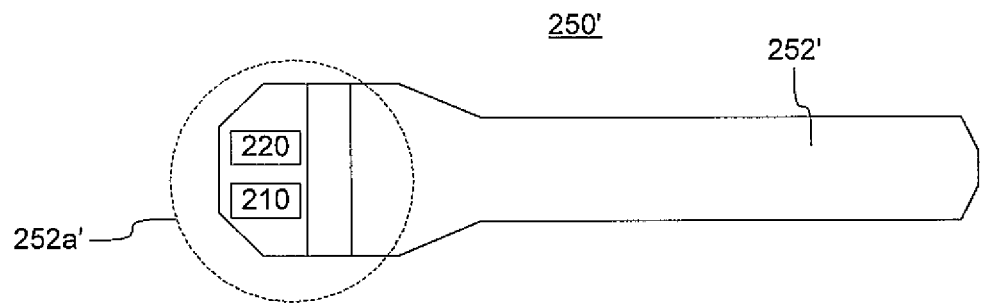
FIGS. 7A and 7B schematically illustrate respective examples of arranging some components of a portable analyzer into a casing.
Figure 7B:
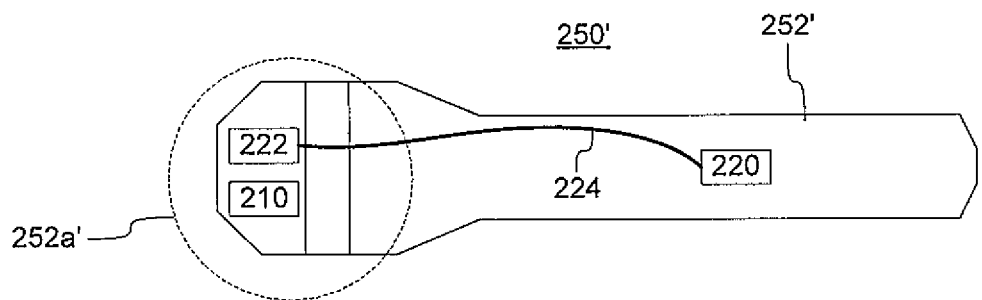

FIGS. 7A and 7B illustrate respective two examples of arranging some components of the portable analyzer 200 in a casing 250'. The illustration of FIG. 6A schematically depicts a side view to the casing 250', which, at least conceptually, includes a single part only: an elongated body 252' that houses at least the excitation means 210, the detector means 220, the analysis means 230 (not shown in FIG. 7A) and the control means 240 (not shown in FIG. 7A). Hence, no specific handle for holding the portable analyzer 200 is provided in the casing 250', but the user is able to operate the portable analyzer 200 by grabbing or holding the device from the body 252' when using the portable analyzer 200. The illustration in FIG. 7B schematically depicts some components of the portable analyzer 200' arranged in the casing 250'. The difference to the example of the illustration of FIG. 7A is the location of the detector means 220, which is arranged close to the middle part of the body 252' instead of being arranged in the front part 252a' as in the illustration of FIG. 7A. Also in this example the front part 252a' comprises the optical receiver 222 that is optically coupled to the detector means 220 by the optical fiber cable 224 or by other suitable means of optical coupling known in the art. The design of the casing 250' may enable providing an analyzer device that is still smaller in size than those depicted in illustrations of FIGS. 6A and 6B without compromising its analysis performance.

Figure 8:
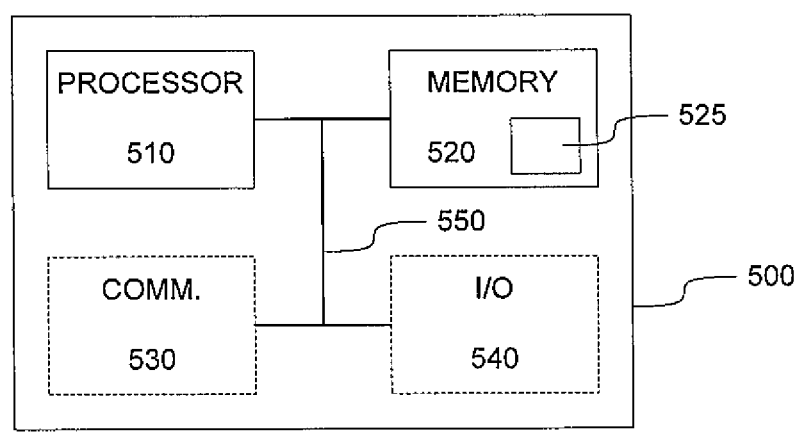
FIG. 8 depicts an apparatus according to an example embodiment.

Each of the analysis means 230 and the control means 240 may be provided by a respective hardware means, by a respective software means or by a respective combination of a hardware means and a software means. As an example in this regard, FIG. 8 schematically depicts some components of an apparatus 500 that may be employed to implement one or more of the analysis means 230 and the control means 240. The apparatus 500 comprises a processor 510 and a memory 520. The memory 520 may store data and computer program code 525. The apparatus 500 may further comprise communication means 530 for wired or wireless communication with other apparatuses and/or user I/O (input/output) components 540 that may be arranged, together with the processor 510 and a portion of the computer program code 525, to provide the user interface for receiving input from a user of the portable analyzer 200, 200' and/or providing output to the user of the portable analyzer 200, 200'. In particular, the user I/O components may include the user input means and/or the user output means referred to in the foregoing. The components of the apparatus 500 are communicatively coupled to each other via a bus 550 that enables transfer of data and control information between the components.

The memory 520 and a portion of the computer program code 525 stored therein may be further arranged, with the processor 510, to provide the control means 240. The processor 510 is configured to read from and write to the memory 520. Although the processor 510 is depicted as a respective single component, it may be implemented as respective one or more separate processing components. Similarly, although the memory 520 is depicted as a respective single component, it may be implemented as respective one or more separate components, some or all of which may be integrated/removable and/or may provide permanent/semi-permanent/dynamic/cached storage.

The computer program code 525 may comprise computer-executable instructions that implement functions of the analysis means 230 and/or the control means 240 when loaded into the processor 510. As an example, the computer program code 525 may include a computer program consisting of one or more sequences of one or more instructions. The processor 510 is able to load and execute the computer program by reading the one or more sequences of one or more instructions included therein from the memory 520. The one or more sequences of one or more instructions may be configured to, when executed by the processor 510, cause the apparatus 500 to operate as the analysis means 230 and/or the control means 240 e.g. according to operations, procedures and/or functions described in the foregoing. Hence, the apparatus 500 may comprise at least one processor 510 and at least one memory 520 including the computer program code 525 for one or more programs, the at least one memory 520 and the computer program code 525 configured to, with the at least one processor 510, cause the apparatus 500 to operate as the analysis means 230 and/or the control means 240 e.g. in accordance with operations, procedures and/or functions described in the foregoing.

The computer program code 525 may be provided e.g. a computer program product comprising at least one computer-readable non-transitory medium having the computer program code 525 stored thereon, which computer program code 525, when executed by the processor 510 causes the apparatus 500 to operate as the analysis means 230 and/or the control means 240 e.g. according to operations, procedures and/or functions described in the foregoing. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described.

Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. A portable analyzer for determining composition of a sample, the portable analyzer comprising:
    a laser source arranged to generate a series of laser pulses for invoking an optical emission from a surface of the sample;
    an adjustable Fabry-Pérot interferometer for observing a selectable wavelength in said optical emission and for recording one or more detection signals that are descriptive of at least one characteristic of said optical emission at a selected wavelength;
    a processor and a memory including computer program code, which when executed by the processor causes the portable analyzer to implement a determination of elemental composition of the sample; and
    a controller for carrying out a spectral analysis for the determination of elemental composition,
    wherein the controller is arranged to carry out the spectral analysis by scanning over a predefined sequence of two or more wavelengths to record respective one or more detection signals at each wavelength of said sequence and analyzing to determine elemental composition of the sample, the spectral analysis being based on the one or more detection signals from the Fabry-Pérot interferometer, said scanning comprising,
    selecting a wavelength of said sequence and adjusting the Fabry-Pérot interferometer to observe said selected wavelength,
    operating the laser source to generate a respective sub-series of laser pulses for invoking the optical emission for recording respective one or more detection signals at said selected wavelength, and
    operating the Fabry-Pérot interferometer to record the respective one or more detection signals at said selected wavelength based on the optical emission invoked by the respective sub-series of laser pulses.

2. A portable analyzer according to claim 1, wherein the Fabry-Pérot interferometer is adjustable to observe said selected wavelength within a first range defined by a predefined minimum wavelength and a predefined maximum wavelength.

3. A portable analyzer according to claim 1, wherein said selected wavelength denotes the center point of a predefined second range of wavelengths, which second range is substantially narrower than the first range.

4. A portable analyzer according to claim 1, wherein the Fabry-Pérot interferometer is adjustable to observe one of two or more predefined wavelengths.

5. A portable analyzer according to claim 1, wherein the Fabry-Pérot interferometer comprises a pair of optical flats arranged in parallel or substantially in parallel to each other and separated from each other by an adjustable air gap, and wherein the selectable wavelength observed by the Fabry-Pérot interferometer is selectable by adjusting the width of said adjustable air gap.

6. A portable analyzer according to claim 1, wherein each sub-series consists of a predefined number of laser pulses.

7. A portable analyzer according to claim 1, wherein said predefined sequence of two or more wavelengths covers wavelengths within a predefined range at predefined intervals.

8. A portable analyzer according to claim 1, wherein said predefined sequence of two or more wavelengths consists of wavelengths that are characteristic to one or more predefined elements.

9. A portable analyzer according to claim 1, wherein said at least one characteristic includes at least one of the following:
  an indication of a presence or absence of radiation at the selected wavelength, and
  an indication of a relative intensity of radiation at the selected wavelength.

10. A portable analyzer according to claim 1, wherein the controller is arranged to display an indication of the determined elemental composition of the sample via a display means provided in the portable analyzer.

11. A method for determining a composition of a sample using a laser source arranged to generate a series of laser pulses for invoking an optical emission from a surface of the sample and an adjustable Fabry-Pérot interferometer for observing a selectable wavelength in said optical emission and for recording one or more detection signals that are descriptive of at least one characteristic of said optical emission at a selected wavelength, the method comprising:
  carrying out a spectral analysis by scanning over a predefined sequence of two or more wavelengths to record respective one or more detection signals at each wavelength of said sequence and analyzing to determine elemental composition of the sample, the spectral analysis being based on the one or more detection signals from the Fabry-Pérot interferometer, wherein said scanning comprises,
  selecting a wavelength of said sequence and adjusting the Fabry-Pérot interferometer to observe the selected wavelength,
  operating the laser source to generate a respective sub-series of laser pulses for invoking the optical emission for recording respective one or more detection signals at said selected wavelength, and
  operating the Fabry-Pérot interferometer to record the respective one or more detection signals at said selected wavelength based on the optical emission invoked by the respective sub-series of laser pulses.

* * * * *